United States Patent [19]

Varma

[11] 4,277,417
[45] Jul. 7, 1981

[54] HYDROCARBON SOLUBLE SULFONATED POLYOLS, ESTERS OF HYDROCARBON SUBSTITUTED $C_4$-$C_{10}$ DICARBOXYLIC ACIDS WITH POLYOLS AND SULFONIC ACID, PROCESSES THEREFOR, AND LUBRICATING COMPOSITIONS THEREOF

[75] Inventor: Vijaya K. Varma, Belle Mead, N.J.

[73] Assignee: Exxon Research & Engineering Co., Florham Park, N.J.

[21] Appl. No.: 124,085

[22] Filed: Feb. 25, 1980

Related U.S. Application Data

[63] Continuation of Ser. No. 385, Dec. 29, 1978, abandoned.

[51] Int. Cl.$^3$ .................. C10M 1/20; C10M 1/40; C07C 143/68
[52] U.S. Cl. .................. 260/456 R; 252/48.2; 252/48.6
[58] Field of Search .................. 252/48.2, 48.6; 44/76; 260/456 R

[56] References Cited

U.S. PATENT DOCUMENTS

| | | | |
|---|---|---|---|
| 2,363,046 | 11/1944 | DeGroote et al. | 260/456 |
| 2,703,808 | 3/1955 | Buchman | 260/456 |
| 2,861,957 | 11/1958 | Cole et al. | 252/334 |
| 3,208,940 | 9/1965 | Owens et al. | 252/48.2 X |
| 3,381,022 | 4/1968 | Le Suer | 260/404.8 |

FOREIGN PATENT DOCUMENTS

| | | | |
|---|---|---|---|
| 453717 | 12/1948 | Canada | 252/48.2 |
| 560092 | 7/1958 | Canada | 252/48.2 |
| 2044837 | 4/1972 | Fed. Rep. of Germany . | |
| 2206219 | 8/1973 | Fed. Rep. of Germany | 44/76 |
| 2044708 | 2/1971 | France . | |

*Primary Examiner*—W. J. Shine
*Attorney, Agent, or Firm*—Roland A. Dexter; Frank T. Johmann

[57] ABSTRACT

Oil-soluble sulfonated polyols and oil-soluble, partially sulfonated polyol ester reaction products of $C_6$-$C_{10,000}$ hydrocarbon substituted $C_4$-$C_{10}$ dicarboxylic acid materials, e.g. alkenyl succinic anhydride, are useful as oil and fuel additives. The polyol esters of dicarboxylic acids have been readily produced under reaction conditions characterized by conducting said reaction in the presence of at least a sediment-reducing amount of a hydrocarbon soluble $C_{12}$-$C_{80}$, preferably a $C_{24}$-$C_{36}$, hydrocarbon substituted sulfonic acid whereby sediment resulting from said reaction is markedly reduced to less than 1 vol. % and filtration of the reaction product is facilitated.

18 Claims, No Drawings

HYDROCARBON SOLUBLE SULFONATED POLYOLS, ESTERS OF HYDROCARBON SUBSTITUTED $C_4$-$C_{10}$ DICARBOXYLIC ACIDS WITH POLYOLS AND SULFONIC ACID, PROCESSES THEREFOR, AND LUBRICATING COMPOSITIONS THEREOF

This is a continuation of application Ser. No. 000,385, filed Dec. 29, 1978, now abandoned.

BACKGROUND OF THE INVENTION

1. Field of the Invention

This invention relates to a process for producing novel hydrocarbon-soluble partially sulfonated polyol ester derivatives of a monoethylenically unsaturated $C_4$-$C_{10}$ dicarboxylic acid material under conditions of reduced sediment formation as well as to the resulting substantially sediment-free product useful for preparing ashless dispersants utilized in lubricating oil and fuel compositions. In particular, this invention is directed to a sediment-free process involving the polyol esterification of alkenyl succinic anhydride to provide lubricating oil and fuel additives wherein said reaction is carried out in the presence of a sediment-reducing amount of an oil-soluble sulfonic acid or with an oil-soluble partially sulfonated polyol. The invention also relates to the sulfonated polyol ester and lubricating oil compositions thereof.

2. Description of the Prior Art

During the past several decades, ashless sludge dispersants have become increasingly important, primarily in improving the performance of lubricants in keeping the engine clean of deposits and permitting extended crankcase oil drain periods while avoiding the undesirable environmental impact of the earlier used metal-containing additives. Most commercial ashless dispersants fall into several general categories.

One category of ashless dispersants involves the esterification product of alkenyl substituted acids, e.g. polyisobutenyl succinic acids, with polyols, e.g. pentaerythritol, as taught in U.S. Pat. No. 3,381,022; however, the usual process of making such a dispersant requires not only an esterification catalyst (such as sulfuric acid, benzene sulfonic acid, p-toluene sulfonic acid, phosphoric acid, etc., see col. 5, lines 68–75) but must be carried out at such an elevated temperature that large amounts, i.e. in the range of 2 to 6 vol.%, of sediment are formed.

Sulfonic acids are also used in other esterification reactions such as: the condensation of polyisobutenyl succinic anhydride with a tetraalkylol urea (see U.S. Pat. No. 3,897,456); sulfonated styrene-divinylbenzene copolymer exchange resin for the esterification of an 8–300 carbon branched chain alkenyl succinic anhydride with a variety of alcohols (see U.S. Pat. No. 4,029,675); and, the reaction of a monocarboxylic acid with a polyol in the presence of methanesulfonic acid (see U.S. Pat. Nos. 4,029,675 and 4,025,447 corresponding to German DAS 2 520 459).

Sulfonate esters of polyols are known (see U.S. Pat. No. 2,703,808 for the reaction product of sulfonyl chlorides and pentaerythritol and U.S. Pat. No. 3,579,630 for disclosure of pentaerythritol tetrakis (p-toluene sulfonate)).

Finally, a fuel additive is reported in U.S. Pat. No. 4,059,414 as the reaction product of an alkyl benzene sulfonate and the derivative of a fatty acid and a trialkanolamine.

SUMMARY OF THE INVENTION

It has been discovered that the problem of sediment formation in the polyol esterification of an alkenyl succinic anhydride, e.g. poly(isobutenyl) succinic anhydride, can be overcome by: incorporating into said esterification environmeent a sediment-reducing amount e.g. 0.1 to 15, preferably 0.2 to 1.5, wt.% of an oil-soluble $C_{12}$-$C_{80}$, preferably $C_{24}$-$C_{36}$, sulfonic acid; or, reacting said anhydride with an oil-soluble partially sulfonated polyol having at least one hydroxy group available for reaction with a carboxyl moiety of said anhydride.

This invention can thus be characterized in one embodiment as a process for the preparation of a partially sulfonated polyol ester of a hydrocarbon-soluble $C_6$-$C_{10,000}$ hydrocarbon substituted $C_4$-$C_{10}$ dicarboxylic acid material, preferably $C_{10}$-$C_{150}$ olefin substituted succinic anhydride, comprising the step of reacting said dicarboxylic acid material, for example, polyisobutylene succinic anhydride, with a polyol (in a mole ratio of 1 to 3, preferably 1 to 2, of dicarboxylic acid material to polyol) in the presence of a sediment-reducing amount, generally from 0.1 to 15, preferably 0.2 to 1.5, wt%, of an oil-soluble sulfonic acid, preferably a $C_{18}$-$C_{30}$ hydrocarbon substituted benzene sulfonic acid, said wt.% based upon the total weight of the reactants. The esterification reaction temperature ranges from 120°–260° C., preferably 140°–230° C. and is for a period of from 1–24 hours, preferably 2–10 hours, optimally from 3–6 hours.

Provided according to this invention is the oil-soluble (both full and partial) $C_{12}$-$C_{80}$ hydrocarbon substituted sulfonate, preferably a $C_{18}$-$C_{30}$ alkyl benzene sulfonate of a polyol, as well as the said sulfonated polyol esters of a $C_6$-$C_{10,000}$ hydrocarbon substituted dicarboxylic acid material, preferably a $C_4$-$C_{10}$ dicarboxylic acid anhydride, optimally succinic anhydride.

Further, it has been discovered that said $C_{12}$-$C_{80}$ hydrocarbon substituted sulfonate of a polyol obtained by this invention has utility as a dispersant for a wide variety of applications such as in a shampoo, cutting oil, etc., but preferably as an additive for lubricants.

Although not known for certain it appears that the sulfonate of a polyol can be represented in part by the formula

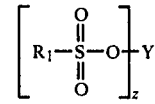

wherein Y represents

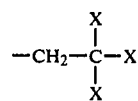

in which X is selected from the group consisting of hydrogen, alkyl, hydroxyalkyl, $OCH_2C(CH_2OH)_3$, $-(CH_2)_nOH$ or $-(CH_2OCH_2CH_2O)_nH$ where n is 1 to 3 and with the restriction that at least one X contains a hydroxy moiety, z represents an integer of from 1 to 8 and $R_1$ is a hydrocarbon substituent containing from 12 to 80 carbons. For the full sulfonate of a polyol every hydroxy moiety is sulfonated.

The novel compounds described above as effective dispersants which are particularly useful in lubricating oil compositions are also highly useful as dispersants in fuel compositions, such as burner fuel compositions, and motor fuel compositions, for example, in gasolines and in diesel fuels.

These novel products of the invention are believed to occur as a result of the reaction of 1.0 mole of a hydrocarbon substituted dicarboxylic acid material with from 1.0 to 3.0, preferably 1.1 to 1.9 moles, of a polyol having about 2 to 8, e.g. 2 to 6 hydroxy groups and containing a total of 2 to 40 carbons in the presence of from 0.1 to 15, preferably 0.2 to 1.5, wt.% of a $C_{12}$ to $C_{80}$ hydrocarbon substituted sulfonic acid whereby the sediment of said reaction is reduced to less than 1 vol.%, all wt.% being based on the total weight of the reactants. An alternative to said reaction is to first sulfonate said polyol by reacting from 1 to 15%, preferably 0.2 to 1.5 wt.%, of said sulfonic acid with said polyol at a temperature from 100° C. to 240° C. e.g. 100° C. to 220° C., preferably 100° to 140° C., for 1 to 4, preferably 1 to 2 hours and admixing with said dicarboxylic acid material for subsequent reaction.

These novel sulfonated polyol esters according to the invention thus can be prepared by heating together dicarboxylic acids, anhydrides or simple esters with a polyol such as pentaerythritol and in the presence of an oil-soluble sulfonic acid such as a $C_{(28\ ave)}$ alkyl benzene sulfonic acid.

DETAILED DESCRIPTION OF THE INVENTION

Dicarboxylic Acid Material

The preparation of a polyol ester of the dicarboxylic acid material preferably involves a reaction of an alkenyl succinic acid analog obtained via the Ene reaction of an olefin with an alpha-beta unsaturated $C_4$ to $C_{10}$ dicarboxylic acid, or anhydrides or esters thereof, such as fumaric acid, itaconic acid, maleic acid, maleic anhydride, dimethyl fumarate, etc. The dicarboxylic acid material can be illustrated by an alkenyl succinic anhydride which may contain a single alkenyl radical or a mixture of alkenyl radicals variously bonded to the cyclic succinic anhydride group, and is understood to comprise such structures as:

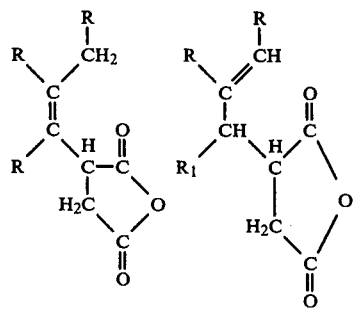

wherein R may be hydrogen or hydrocarbon or substituted hydrocarbon containing from 1 to about 10,000 and more carbons with the restriction that at least one R has at least 6 carbons, preferably from 10 to 150 carbons and optimally from about 60 to about 100 carbons. The anhydrides can be obtained by well-known methods, such as the reaction between an olefin and maleic anhydride or halosuccinic anhydride or succinic ester. In branched olefins, particularly branched polyolefins, R may be hydrogen, methyl or a long chain hydrocarbon group. However, the exact structure may not always be ascertained and the various R groups cannot always be precisely defined in the Ene products from polyolefins and maleic anhydride.

Suitable olefins include butene, isobutene, pentene, decene, dodecene, tetradecene, hexadecene, octadecene, eicosene, and polymers of propylene, butene, isobutene, pentene, decene and the like, and halogen-containing olefins. The olefins may also contain cycloalkyl and aromatic groups. The most preferred alkenyl succinic anhydrides used in this invention are those in which the alkenyl group contains a total of from 6 to 10,000 carbon atoms; and, at least 10 to 150 and more preferably 60 to 100 for mineral oil systems.

Many of these hydrocarbon substituted dicarboxylic acid materials and their preparation are well known in the art as well as being commercially available, e.g., 2-octadecenyl succinic anhydride and polyisobutenyl succinic anhydride.

With 2-chloromaleic anhydride and related acylating agents, alkenylmaleic anhydride reactants are formed.

Preferred olefin polymers for reaction with the unsaturated dicarboxylic acids are polymers comprising a major molar amount of $C_2$ to $C_5$ monoolefin, e.g., ethylene, propylene, butylene, isobutylene and pentene. The polymers can be homopolymers such as polyisobutylene, as well as copolymers of two or more of such olefins such as copolymers of ethylene and propylene; butylene and isobutylene; propylene and isobutylene; etc. Other copolymers include those in which a minor molar amount of the copolymer monomers, e.g., 1 to 20 mole % is a $C_4$ to $C_{18}$ non-conjugated diolefin, e.g., a copolymer of isobutylene and butadiene; or a copolymer of ethylene, propylene and 1,4-hexadiene; etc.

The olefin polymers will usually have number average molecular weights ($\overline{M}_n$) within the range of 700 and about 140,000; more usually between about 900 and about 10,000. Particularly useful olefin polymers have ($\overline{M}_n$) within the range of about 1200 and about 5000 with approximately one terminal double bond per polymer chain. An especially valuable starting material for a highly potent dispersant additive are polyalkenes e.g. polyisobutylene, having about 90 carbons.

Especially useful when it is desired that the dispersant additives also possess viscosity index improving properties are 5,000 to 200,000 e.g., 25,000 to 100,000 number average molecular weight polymers. An especially preferred example of such a V.I. improving polymer is a copolymer of about 30 to 85 mole % ethylene, about 15 to 70 mole % $C_3$ to $C_5$ mono-alpha-olefin, preferably propylene, and 0 to 20 mole % of a $C_4$ to $C_{14}$ non-conjugated diene.

These ethylene-propylene V.I. improving copolymers or terpolymers are usually prepared by Ziegler-Natta synthesis methods. Some of these copolymers and terpolymers are commercially available such as VISTALON ®, an elastomeric terpolymer of ethylene, propylene and 5-ethylidene norbornene, marketed by Exxon Chemical Co., New York, NY and NORDEL ®, a terpolymer of ethylene, propylene and 1,4-hexadiene marketed by E. I. duPont de Nemours & Co.

The Polyol

The polyhydric alcohol used to react with the dicarboxylic acid material and/or the hydrocarbyl sulfonic acid can have 2 to 8 hydroxy groups and a total of 2 to 40 carbon atoms and can be represented by the formula:

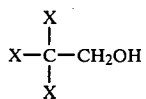

wherein X is hydrogen, an alkyl, hydroxy alkyl, $-OCH_2C(CH_2OH)_3$, $-(CH_2)_nOH$, or $-(CH_2OCH_2CH_2O)_nH$ wherein n is 1 to 3 with at least one of the X substituents being a hydroxy alkyl group and preferably all of the X substituents being a hydroxy alkyl group of the structure $-(CH_2)_nOH$, wherein n is 1 to 3.

Examples of such polyols are illustrated by ethylene glycol, diethylene glycol, triethylene glycol, tetraethylene glycol, dipropylene glycol, tripropylene glycol, dibutylene glycol, tributylene glycol, and other alkylene glycols in which the alkylene group contains from two to about eight carbon atoms. Other useful polyhydric alcohols include glycerol, monooleate of glycerol, monostearate of glycerol, monomethyl ether of glycerol, pentaerythritol, 9,10-dihydroxy stearic acid, methyl ester of 9,10-dihydroxy stearic acid, 1,2-butanediol, 2,3-hexanediol, 2,4-hexanediol, pinacol, erythritol, arabitol, sorbitol, mannitol, 1,2-cyclohexanediol, and xylene glycol. Carbohydrates such as sugars, starches, celluloses, etc., likewise may yield the esters of this invention. The carbohydrates may be exemplified by glucose, fructose, sucrose, rhamnose, mannose, glyceraldehyde, and galactose.

An especially preferred class of polyhydric alcohols are those having at least three hydroxyl groups, such as pentaerythritol, dipentaerythritol, tripentaerythritol, sorbitol and mannitol. Solubility of some polyhydric alcohols may be increased by esterifying some of the hydroxyl groups with a monocarboxylic acid having from about 8 to about 30 carbon atoms such as octanoic acid, oleic acid, stearic acid, linoleic acid, dodecanoic acid, or tall oil acid. Examples of such partially esterified polyhydric alcohols are the monooleate of sorbitol, distearate of sorbitol, monooleate of glycerol, monostearate of glycerol, and dodecanoate of erythritol. Because of its effectiveness, availability, and cost, pentaerythritol is particularly preferred.

Sulfonic Acid

According to this invention, the reactant for inhibiting sediment formation is the oil-soluble sulfonic acids which are typically alkaryl sulfonic acids. These sulfonic acids are typically obtained by the sulfonation of alkyl substituted aromatic hydrocarbons such as those obtained from the fractionation of petroleum by distillation and/or extraction or by the alkylation of aromatic hydrocarbons as, for example, those obtained by alkylating benzene, toluene, xylene, naphthalene, diphenyl and the halogen derivatives such as chlorobenzene, chlorotoluene and chloronaphthalene. The alkylation may be carried out in the presence of a catalyst with alkylating agents having from about 3 to about 70 carbon atoms such as, for example, haloparaffins, olefins that may be obtained by dehydrogenation of paraffins, polyolefins as, for example, polymers from ethylene, propylene, etc. Preferred sulfonic acids are those obtained by the sulfonation of hydrocarbons prepared by the alkylation of benzene or toluene with tri-, tetra- or pentapropylene fractions obtained by the polymerization of propylene. The alkaryl sulfonates contain from 12 to 80 carbon atoms, preferably from 18 to 30 carbon atoms per alkyl substituted aromatic moiety. Particularly preferred is a $C_{28\ ave}$ alkyl benzene sulfonic acid having a molecular weight of about 550.

The alkylated benzene from which the sulfonic acid is prepared is obtained by known alkylation processes; benzene being generally reacted with such alkylating agents as isobutylene, isoamylene, diisobutylene, triisobutylene, etc., or olefin mixtures containing from refinery gases. Boron trifluoride is a preferred alkylating agent.

Esterification Conditions

As discussed, the sulfonated polyol esters of the invention may be readily prepared by one of several methods. The method which is preferred because of the superior properties of the esters it produces and the reduced formation of sediment can be effected by adding together 1 to 3, preferably 1.1 to 1.9 mole of the said polyol per mole of the dicarboxylic acid material with or without inert diluent and heating with from 0.2 to 1.5 wt.% of a hydrocarbon substituted sulfonic acid of 24 to 36 carbons at 120°–260° C., preferably 140°–230° C. until reaction is complete by infrared analysis of the product showing maximal absorption for ester.

The water formed as a by-product is removed by distillation as the esterification proceeds. A solvent may be used in the esterification to facilitate mixing and temperature control. It also facilitates the removal of water from the reaction mixture. The useful solvents which are inert solvents in the above reaction include hydrocarbon oils, e.g. mineral lubricating oil, kerosene, neutral mineral oils, xylene, halogenated hydrocarbons, e.g., carbon tetrachloride, dichlorobenzene, tetrahydrofuran, etc.

The relative proportions of the polyhydroxy reactant to the dicarboxylic acid material reactant depend to a large measure upon the type of the product desired and the number of hydroxyl groups present in the molecule of the hydroxy reactant. For instance, the formation of an ester of the dicarboxylic acid, i.e., one in which the acid radical is esterified, involves the use of about one mole of the partially sulfonated polyol for each mole of dicarboxylic acid.

This invention has made it possible to increase the proportion of the polyhydric alcohol, e.g. pentaerythritol which can be used with the dicarboxylic acid material, e.g. a $C_{90}$ alkenyl succinic anhydride. Previously the pentaerythritol had been practically limited to about 1.1 mole per mole of anhydride. With the invention it becomes possible to react from 2 to 3 moles of the partially sulfonated polyol with one mole of anhydride. For the purposes of this invention, it has been found that esters obtained by the reaction of one equivalent of the dicarboxylic acid reactant to 2 molar amounts of the sulfonated hydroxy reactant have superior properties and are therefore preferred.

Another approach to esterification is to first produce the partial sulfonate of the polyol and thereafter react this compound with the dicarboxylic acid material generally as above. The method for producing the partial sulfonate of the polyol involves reacting 1 to 3 moles of said sulfonic acid per mole of said polyol at a temperature of 120° to 140° C. for 2 to 4 hours.

USE OF THE SULFONATED POLYOL ESTER ADDITIVE IN OLEAGINOUS COMPOSITIONS

The hydrocarbon-soluble sulfonated polyol ester reaction products of the invention can be incorporated in a wide variety of oleaginous compositions for sludge and varnish control. They can be used in lubricating oil compositions, such as automotive crankcase lubricating oils, automatic transmission fluids, etc., in concentrations generally within the range of about 0.01 to 20 wt.%, e.g. 0.1 to 10 wt.%, preferably 0.3 to 3.0 wt.%, of the total composition. The lubricants to which the sulfonated polyol ester products can be added include not only hydrocarbon oils derived from petroleum but also include synthetic lubricating oils such as polyethylene oils; alkyl esters of dicarboxylic acid; complex esters of dicarboxylic acid, polyglycol and alcohol; alkyl esters of carbonic or phosphoric acids; polysilicones; fluorohydrocarbon oils; mixtures of mineral lubricating oil and synthetic oils in any proportion, etc.

When the products of this invention are used as multifunctional additives having detergent and antirust properties in petroleum fuels such as gasoline, kerosene, diesel fuels, No. 2 fuel oil and other middle distillates, a concentration of the additive in the fuel in the range of 0.001 to 0.5 weight percent, based on the weight of the total composition, will usually be employed.

When used as an antifoulant in oleaginous, e.g. mineral oil, streams in refinery operations to prevent fouling of process equipment such as heat exchangers or in turbine oils, about 0.001 to 2 wt.% will generally be used.

The additive may be conveniently dispensed as a concentrate comprising generally a proportion of the additive, e.g. 20 to 90 parts by weight, dissolved in a mineral lubricating oil, e.g., 10 to 80 parts by weight, with or without other additives being present.

In the above compositions or concentrates, other conventional additives may also be present including dyes, pour point depressants, antiwear agents such as tricresyl phosphate or zinc dialkyldithiophosphates of 3 to 8 carbon atoms in each alkyl group, antioxidants, such as N-phenyl α-naphthylamine, tert-octylphenol sulfide, 4,4-methylene bis(2,6-di-tert-butyl phenol), viscosity index improvers such as ethylene-propylene copolymers, polymethacrylates, polyisobutylene, alkyl fumarate-vinyl acetate copolymers and the like, deemulsifiers such as polysiloxanes, ethoxylated polymers and the like.

This invention will be further understood by reference to the following examples, which include preferred embodiments of the invention.

EXAMPLE 1

A fifty-gallon glass-lined reactor provided with a stirrer was first charged with 96 pounds of polyisobutylene succinic anhydride of number average molecular weight ($\overline{M}_n$) of about 1300 (carbon chain lengths of substituent hydrocarbon group of 35 to 700 carbons) dissolved in an equal weight of mineral oil. The charge was heated to 218° C. and 13.2 pounds of pentaerythritol added with stirring. The total charge was soaked at 218° C. for 3 hours after which it was stripped with nitrogen for 1 hour and then allowed to cool at 160° C. after which the system was filtered through a sparkler filter. The product had a viscosity at 100° C. of 2688 SUS with 2.2 volume percent sediment and a haze of 60 neph. prior to filtering and a sediment of 0.08 volume % after filtering and a haze reading of 36 nephelos.

EXAMPLE 2

The process of Example 1 was followed except that 2.2 pounds (1.0 weight percent) of a mineral oil solution containing 50 percent by weight of a $C_{28}$–$C_{32}$ monoalkyl benzene sulfonic acid having a ($\overline{M}_n$) of 550 was added with the pentaerythritol and the temperature of reaction was kept at 190° C.

The resulting product had a kinematic viscosity @100° C. of 2432 SUS with 0.2 volume percent sediment and haze of 20 neph. prior to filtration and only a trace (<<0.01 volume percent) of sediment and haze of 15 nephelos after filtration.

EXAMPLE 3

The process of Example 2 was followed except 22.7 pounds of pentaerythritol and 9.3 pounds of said mineral oil solution containing said sulfonic acid was used. The resulting product had a kinematic viscosity @100° C. of 7656 SUS and a sediment of 0.6 volume percent prior to filtration.

Engine Test Results of Additives

EXAMPLE 4

Three formulated lubricating oil blends were prepared by blending 3.5 percent of the concentrate of Examples 1, 2 and 3 with a lubricating oil blend of two neutral base oils and formulated with a metal detergent (calcium sulfonate overbased to a 400 TBN) and zinc dialkyl dithiophosphate to provide a formulated lubricating oil.

Each of the blends prepared as described above was subjected to the MS Sequence VC Engine Test which is a test well known in the automotive industry. The test is run in a Ford engine of 302 cubic inch displacement following the procedure described in the publication entitled "Multi-Cylinder Test Sequences for Evaluating Automotive Engine Oil" (ASTM Special Publication 315-E). At the end of each test, various parts of the engine are rated on a merit basis wherein 10 represents a perfectly clean part, and lesser numbers represent increasing degrees of deposit formation. The various ratings are then totaled and averaged on the basis of 10 as a perfect (completely clean) rating. The results obtained with the three blends described above are given in Table I.

TABLE I

MS SEQUENCE VC TEST RESULTS
MERIT RATINGS (BASIS 10)

|  | 3.5 wt. % Product of Ex. 1 | 3.5 wt. % Product of Ex. 2 | 3.5 wt. % Product of Ex. 3 | Passing Limits For SE Quality Oils |
|---|---|---|---|---|
| Sludge | 9.18 | 8.97 | 9.46 | 8.5 |
| Ave. Varnish Piston Skirt | 8.17 | 8.47 | 8.24 | 8.0 |
| Varnish | 7.04 | 7.88 | 7.62 | 7.9 |

Product is 50% active ingredient in oil

EXAMPLES 5-8

In laboratory preparations of the pentaerythritol ester of polyisobutenyl succinic anhydride, the molar ratio of the former to the latter was compared in ascertaining the overall influence of the presence of varying amounts of an oil-soluble $C_{(28\ ave)}$ alkyl benzene sulfonic acid as well as variations in the molar ratio.

In each of the reactions 1 mole of polyisobutenyl succinic anhydride of ($\overline{M}_n$) of 1300 is reacted with varying amounts of pentaerythritol (from 1 to 2.1 moles) and varying amounts of long chain alkyl benzene sulfonic acid.

The results of these several reactions are shown in the following Table.

TABLE II

| Example | Mole Ratio of PIBSA:PE | $C_{28\ ave}$ alkyl benzene sulfonic acid wt. % | Time of Reaction hrs. | Temperature of Reaction °C. | Sediment Prior to Filtration Vol % |
|---|---|---|---|---|---|
| 5 | 1:1 | 0 | 6 | 145 | 5 |
| 6 | 1:1.1 | 14.3 | 0.5 | 145 | 2 |
| 7 | 1:1.5 | 13.7 | 0.5 | 145 | 0.5 |
| 8 | 1:2 | 14.0 | 0.5 | 145 | 0.18 |

EXAMPLE 9

One equivalent of polyisobutenyl succinic anhydride (PIBSA) of ($\overline{M}_n$) of 1300, 1 equiv. of $C_{28\ ave}$ sulfonic acid (S.A.), 1.1 equivalent of pentaerythritol and Coray oil (enough to have 50% active ingredient) was heated to 140° C. in a four-necked flask fitted with a stirrer, nitrogen sparger, and a thermometer. The reaction mixture is held at 140° C. for 2 hours, at the end of which the contents are filtered hot through 1" thick layer of celite. Total acid number 2.55, Percentage of free sulfonic acid 0.2%, Sediment 0.1 Vol. percent.

EXAMPLE 10

In a four-necked flask fitted with a stirrer, nitrogen sparger and a thermometer was charged one equivalent of (S.A.) and 1.1 equivalent of pentaerythritol (and Coray oil to have 50% AI) and heated at 140° C. for 2 hours. To this was added 50% oil solution of one equivalent of PIBSA (same as above) and heated with nitrogen sparging for 2 hours. The product was filtered hot through 1" celite. The product was identical in structure to the above product.

EXAMPLE 11

One equivalent of PIBSA and varying amounts of pentaerythritol (PE) and $C_{28\ ave}$ alkyl benzene sulfonic acid (S.A.) are diluted with Coray oil to give 50% active ingredient. The mixtures were each heated in a four-necked flask fitted with a stirrer, thermometer and nitrogen sparger to 211° C. in 0.5 hr. and maintained at 210° C. for 3 hours with nitrogen stripping then cooled to 140° C. and filtered through 1" celite. Sediment levels are shown in the Table III for the various runs.

TABLE III

| Reaction No. | PIBSA (equiv.) | PE (equiv.) | SA (equiv.) | Vol. % |
|---|---|---|---|---|
| 11-1 | 1 | 1.9 | 0.03 | 6 |
| 11-2 | 1 | 1.9 | 0.05 | 6–8 |
| 11-3 | 1 | 1.9 | 0.1 | 0.8 |
| 11-4 | 1 | 1.9 | 0.3 | 0.07 |
| 11-5 | 1 | 1.9 | 0.5 | 0.04 |
| 11-6 | 1 | 1.9 | 1 | 0.01 |
| 11-7 | 1 | 2 | 2 | 0.0 |
| 11-8 | 1 | 1.5 | 1 | 0.2 |
| 11-9 | 1 | 1.1 | 0.02 | 0.21 |
| 11-10 | 1 | 1.1 | 0.1 | .5 |
| 11-11 | 1 | 1.1 | 0.2 | 0.3 |
| 11-12 | 1 | 1.1 | 0.3 | 0.05 |
| 11-13 | 1 | 1.1 | 1 | .01 |

EXAMPLE 12

430 grams of polyisobutenyl succinic anhydride of ($\overline{M}_n$) of about 1300 and 170 grams of Solvent 150 Neutral mineral oil were added to a 1000 ml. 4-necked flask fitted with a stirrer and heated to 218° C. at which time 41.4 grams of pentaerythritol was added. The reactants were kept at 218° C. for 1.5 hours with stirring and under a nitrogen sparge at rate of 80 cc 1 min. At this point 1.2 grams of p-toluene sulfonic acid was slowly added and the reaction continued for 1.5 hours at 218° C. with continued nitrogen sparging.

After cooling, the sediment volume was found to be 1.8 volume percent.

In three subsequent runs, the above procedure was altered to introduce the p-toluene sulfonic acid with the addition of the pentaerythritol (PE).

(a) When 6 grams was introduced there was such violent spattering and foaming that the reaction could not be continued.

(b) When 3 grams of p-toluene sulfonic acid was introduced along with the PE at 175° C. and the temperature then raised to 220° C. over 1.5 hours the foaming and violence was tolerable. After 5 hours reaction at 220° C. the resulting sediment was measured at 3.6 vol. %.

(c) The procedure of 12(b) was followed with 4.4 vol. % sediment obtained.

The oil-soluble partially sulfonated polyols of the invention can be reacted with monocarboxylic acids and polycarboxylic (e.g tricarboxylic) acids as well as with dicarboxylic acid materials to yield products with dispersant activity.

Particularly useful monocarboxylic acids include oleic, lauric, myristic, palmitic, stearic and those containing longer carbon chains since all of these acids after esterification with said sulfonated polyols have dispersant activity in oleaginous compositions. Representative of polycarboxylic acids are 2-(3-carboxypropyl)-1,1,5,6-heptanetetracarboxylic acid, 2,3,5-hexanetricarboxylic acid and 1,3,5-naphthalene tricarboxylic acid. Further, these mono- and polycarboxylic acids can be reacted with said polyols in the presence of said oil-soluble $C_{12}$–$C_{80}$ sulfonic acid to produce the related sulfonate esters of said mono- or polycarboxylic acids with comparable utility as dispersants for oleaginous compositions.

The invention in its broader aspect is not limited to the specific details shown and described and departures may be made from such details without departing from the principles of the invention and without sacrificing its chief advantages.

What is claimed is:

1. A hydrocarbon soluble partial sulfonate of a polyol comprising the product obtained from heating together a mixture consisting essentially of a polyol having at least three and up to eight hydroxy groups and containing a total of 2 to 40 carbons and a hydrocarbon soluble $C_{12}$–$C_{80}$ hydrocarbyl substituted sulfonic acid at a temperature of from 100°–240° C. until sulfonation is complete by infrared analysis and/or cessation of water evolution.

2. A product according to claim 1 wherein said polyol is pentaerythritol and said sulfonic acid is alkyl benzene sulfonic acid having an average of about 28 carbons in said alkyl.

3. A hydrocarbon soluble partially sulfonated polyol ester reaction product comprising the reaction product obtained by heating together a $C_6$–$C_{10,000}$ hydrocarbon substituted $C_4$–$C_{10}$ dicarboxylic acid material with a polyol having at least three and up to eight hydroxy groups and containing 2 to 40 carbons in a molar ratio range of said dicarboxylic acid material to said polyol of 1 to 1 to 1 to 3 and in the presence of at least a sediment-reducing amount of a $C_{12}$–$C_{80}$ hydrocarbon substituted sulfonic acid, said reaction conducted at a temperature of from 120°–260° C. until esterification is complete by infrared analysis and/or cessation of water evolution.

4. A product according to claim 3 wherein said dicarboxylic acid material is an alkenyl succinic anhydride, said polyol is of the formula

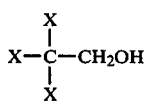

wherein X is hydrogen, alkyl or hydroxy alkyl, said alkyl groups having 1 to 3 carbon atoms, and at least one of said X is a hydroxy alkyl group of the structure —$(CH_2)_n$OH where n is 1 to 3 and said sulfonic acid is present in an amount ranging from 0.1 to 15 wt. % based on the total weight of said reactants.

5. A product according to claim 4 wherein said anhydride is polyisobutenyl succinic anhydride having a ($\overline{M}_n$) of from 900 to 10,000, said polyol is pentaerythritol, said sulfonic acid is alkyl benzene sulfonic acid having an average of about 28 carbons in said alkyl and present in an amount ranging from 0.2 to 1.5 wt. %.

6. A lubricating oil composition comprising a major amount of lubricating oil and at least a dispersing amount of the oil soluble product obtained from heating together a mixture of a polyol having at least three and up to eight hydroxy groups and containing a total of 2 to 40 carbons, and a hydrocarbon soluble $C_{12}$–$C_{80}$ hydrocarbyl substituted sulfonic acid at a temperature of from 100°–220° C. until sulfonation is complete by infrared analysis and/or cessation of water evolution.

7. A lubricating oil composition comprising a major amount of lubricating oil and at least a dispersing amount of the oil soluble product obtained by heating together a $C_6$–$C_{10,000}$ hydrocarbyl substituted $C_4$–$C_{10}$ dicarboxylic acid material with a polyol having at least three and up to eight hydroxy groups and containing 2 to 40 carbons in a molar ratio range of said dicarboxylic acid material to said polyol of 1 to 1 to 1 to 3 and in the presence of from 0.2 to 1.5 wt. % of a $C_{12}$–$C_{80}$ hydrocarbon substituted sulfonic acid, said wt. % based on the total weight of said reactants.

8. An additive concentrate comprising an amount of lubricating oil in the range of 10 to 80 parts by weight, and 20 to 90 parts by weight of an oil-soluble product obtained by heating together a $C_6$–$C_{10,000}$ hydrocarbyl substituted $C_4$–$C_{10}$ dicarboxylic acid material with a polyol having at least three and up to eight hydroxy groups and containing 2 to 40 carbons in a molar ratio range of said dicarboxylic acid material to said polyol of 1 to 1 to 1 to 3 and in the presence of from 0.2 to 1.5 wt. % of a $C_{12}$–$C_{80}$ hydrocarbon substituted sulfonic acid.

9. A process for reducing the sediment in the polyol esterification of a $C_6$–$C_{10,000}$ hydrocarbon substituted $C_4$–$C_{10}$ dicarboxylic acid material, wherein said polyol has at least three hydroxy groups and 2 to 40 carbon atoms, characterized by the step of conducting said esterification in the presence of from 0.1 to 15 wt. % of a hydrocarbon-soluble $C_{12}$–$C_{80}$ hydrocarbon substituted sulfonic acid whereby sediment resulting from said reaction is markedly reduced to less than 1 volume percent.

10. A process according to claim 9, wherein the hydrocarbon substituent of said hydrocarbon substituted $C_4$–$C_{10}$ dicarboxylic acid material is a $C_2$ to $C_5$ monoolefin polymer of about 900 to 10,000 number average molecular weight.

11. A process according to claim 10, wherein said hydrocarbon substituted dicarboxylic acid material is alkenyl succinic anhydride.

12. A process according to claim 11, wherein said alkenyl succinic anhydride is polyisobutenyl succinic anhydride.

13. A process according to claim 12, wherein said polyol is a pentaerythritol.

14. A process according to claim 13, wherein said sulfonic acid is alkaryl sulfonic acid having an alkyl group of about 18 to 30 carbon atoms.

15. A process according to claim 14, wherein said sulfonic acid is alkyl benzene sulfonic acid wherein said alkyl group contains an average of about 28 carbon atoms.

16. A hydrocarbon soluble sulfonate of a polyol having at least three and up to eight hydroxy groups and 2 to 40 carbons and a $C_{18}$ to $C_{30}$ alkyl aryl sulfonic acid.

17. A sulfonate according to claim 16, which is a partial sulfonate wherein at least one hydroxy group remains unreacted.

18. A sulfonate according to claim 16, wherein all of the hydroxy groups of the polyol are reacted with said sulfonic acid.

* * * * *